(12) United States Patent
Amann et al.

(10) Patent No.: US 8,026,105 B1
(45) Date of Patent: Sep. 27, 2011

(54) QUANTIFICATION OF LUBRICANT REACTIVITY USING CONSTANT VOLUME COMBUSTION DEVICE

(75) Inventors: Manfred Amann, San Antonio, TX (US); Terrence F. Alger, II, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 12/755,190

(22) Filed: Apr. 6, 2010

(51) Int. Cl.
  *G01N 33/00* (2006.01)
  *G01N 33/26* (2006.01)
  *G01L 23/22* (2006.01)
  *G01L 23/00* (2006.01)

(52) U.S. Cl. ... 436/155; 73/53.01; 73/53.05; 73/114.01; 73/114.05; 73/114.55; 73/114.56

(58) Field of Classification Search ............... 436/155; 508/383, 382, 110; 123/1 A, 275, 274, 253, 123/299, 294; 73/53.01, 53.05, 114.01, 114.05, 73/114.55, 114.56
See application file for complete search history.

(56) References Cited

U.S. PATENT DOCUMENTS

| | | | |
|---|---|---|---|
| 4,251,870 A * | 2/1981 | Jaffe | 700/268 |
| 6,074,444 A * | 6/2000 | Bingley | 44/320 |
| 7,262,155 B2 | 8/2007 | Ryan et al. | |
| 7,389,752 B2 | 6/2008 | Alger et al. | |
| 2004/0242436 A1 * | 12/2004 | Ryan et al. | 508/382 |

OTHER PUBLICATIONS

Shen et al., A Study of the Ignition of n-Heptane, n-Decane, n-Dodecane, and n-Tetradecane at Elevated Pressures, Energy & Fuels, 2009, 23, 2482-2489.*
Ryan et al.,, Fuel Requirements for HCCI Engine Operation, SAE, 2003-1-1813 at JSAE/SAW International Spring Fuels & Lubricants Meeting, Yokohama, Japan, May 19-22, 2003.*

* cited by examiner

*Primary Examiner* — Christine T Mui
(74) *Attorney, Agent, or Firm* — Ann C. Livingston

(57) ABSTRACT

A method for identifying a lubricant composition that reduces the propensity for knock in an engine. The lubricant composition is mixed with a solvent to reduce the viscosity of the lubricant composition, thereby forming a lubricant-solvent mixture having a viscosity similar to or less than that of engine fuel. A sample of a lubricant-solvent mixture is then subjected to a constant volume combustion test to determine the reactivity associated with the lubricant-solvent mixture. The test is repeated for a range of lubricant-solvent ratios, and statistical methods are used to calculate the reactivity of the lubricant composition without solvent.

14 Claims, 3 Drawing Sheets

QUANTIFICATION OF LUBRICANT REACTIVITY USING CONSTANT VOLUME COMBUSTION DEVICE

TECHNICAL FIELD OF THE INVENTION

This invention relates to internal combustion engines, and more particularly to testing lubricants used with such engines.

BACKGROUND OF THE INVENTION

Engine knock (also called detonation or pinging) occurs in a flame propagation engine when one or more pockets of air/fuel mixture explode outside the envelope of the normal combustion front. This auto ignition occurs rapidly, possibly creating a detonation wave that leads to an audible ping or knock. This knock phenomena is affected by the engine's intake manifold pressure, the engine compression ratio, and the spark advance. All of these factors affect engine performance, emissions, and efficiency.

Engine lubricating oil can contribute to knock when used either as a fuel or conventionally for lubrication. For example, U.S. Pat. No. 7,389,752, entitled "Use of Engine Lubricant as Ignition Fuel for Micro-Pilot Ignition System of an Internal Combustion Engine, to Terrence Alger, et al., describes the use of lubricating oil as fuel in a pilot ignition system. U.S. Pat. No. 7,262,155, entitled "High Octane Lubricants for Knock Mitigation in Flame Propagation Engines", to Thomas Ryan, et al, describes how engine lubricant oil may be formulated to reduce knock when used conventionally to coat the engine cylinders.

There is much research directed toward reducing knock. Compositions of fuels and lubricants and methods to prevent or reduce such knock in flame propagation engines are highly desirable. Engine-based testing is one approach to determining the effect of lubricant oils on knock. However, this type of testing is expensive and can introduce complicating factors such as oil consumption and heat transfer.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

DETAILED DESCRIPTION OF THE INVENTION

The following description is directed to testing engine lubricating oils and their additives using a constant volume combustion test device. A typical engine lubricating oil composition (herein referred to as a "lubricant composition") comprises a base lubricant, which may be either petroleum (mineral) based or synthetic, and may also contain one or more additive components. The additive components can include organometallics used for wear prevention, friction reduction, and acid neutralization, various viscosity modifiers, dispersants, and detergents.

Figure 1:
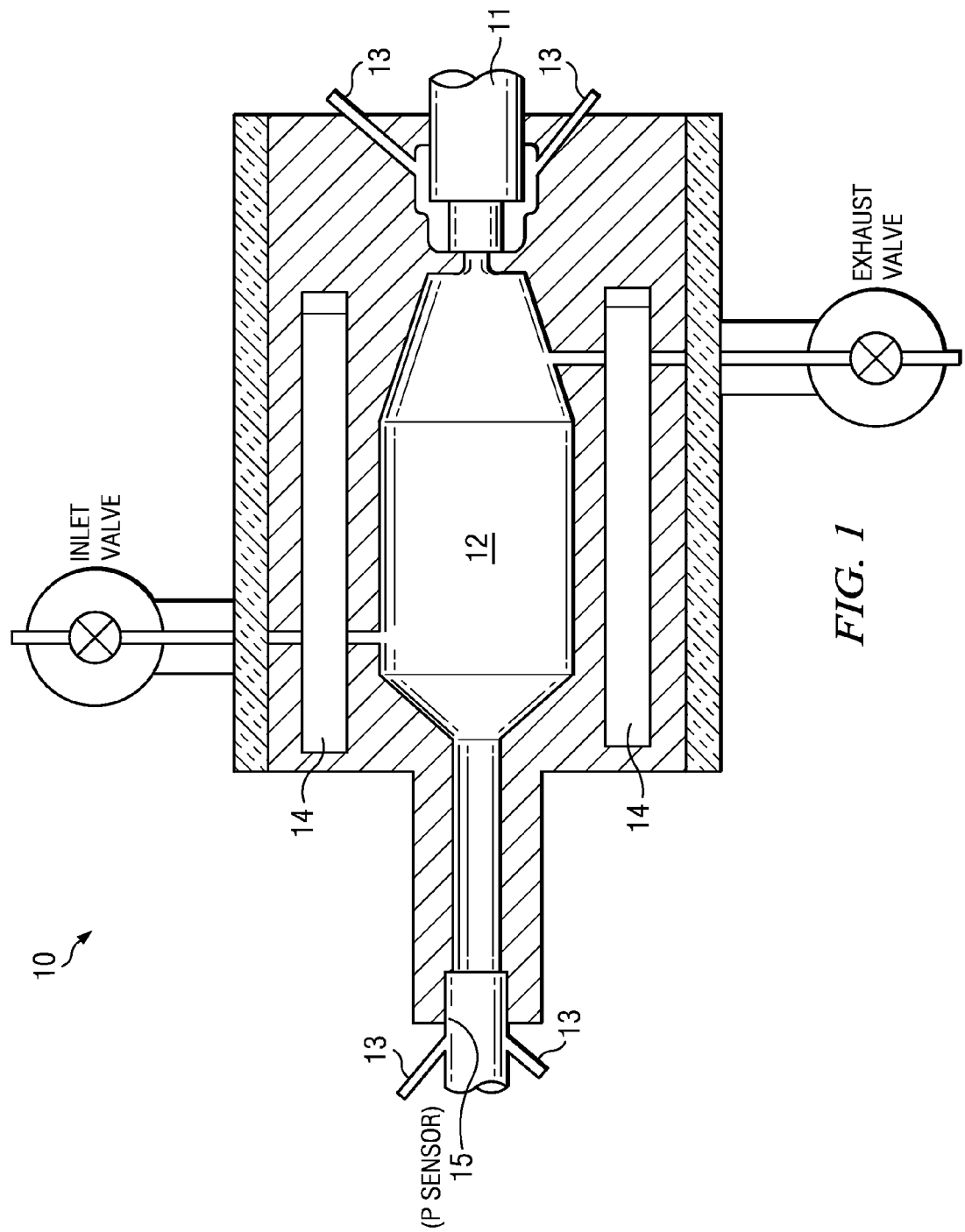
FIG. 1 illustrates a constant volume combustion device used for testing lubricant compositions in accordance with the invention.

FIG. 1 illustrates an example of a constant volume combustion test device 10, used for testing engine lubricant compositions in accordance with the invention. A commercially available example of such a device 10 is the automated Ignition Quality Tester (IQT™), which is typically used to test for the ignition quality of diesel and other fuels. For such applications, device 10 measures the ignition delay and calculates a derived cetane number (CN) of diesel and alternative fuels (including cetane improved diesel fuels. A high cetane number indicates the ability of a diesel engine fuel to ignite quickly after being injected into the combustion chamber.

The constant volume combustion device 10 has a fuel injector 11, which injects an atomized combustible test fluid into a combustion chamber 12. In the course of a test, the air in the vessel is heated and raised to high pressures, similar to the conditions found in a high compression ratio engine. The test fluid is injected using a diesel-style injector and the time period between fuel injection and combustion (the ignition delay) is measured. As stated above, in conventional applications, which test for the ignition quality of a fuel, at a given initial temperature and pressure, that time delay can be related to the CN of the fuel.

Device 10 has coolant paths 13 for cooling the injector and pressure measurement areas. Heating elements 14 provide the heat required for combustion inside chamber 12. A pressure sensor 15 measures pressure in the chamber 12 so that the time between needle lift (fuel injection) and combustion pressure can be measured. Various temperature sensors are used to ensure desired simulation of engine operating conditions.

For purposes of the present invention, the propensity of an engine lubricant composition to affect knock is referred to as its "reactivity". A low reactivity is a desirable characteristic in terms of a lubricant composition's ability to improve the knock resistance of an engine. The constant volume combustion device 10 is used to determine whether a lubricant composition meets the low reactivity criteria that may make it improve knock resistance.

A feature of using device 10 for testing lubricating oils and their components is that the fuel injector 11 is sensitive to the test fluid's viscosity. High viscosity fluids result in poor atomization and mixing. To overcome this problem, the test lubricant composition is dissolved in a combustible solvent. The result is a lubricant-solvent mixture having a viscosity comparable to that of fuels used for internal combustion engines. By measuring the reactivity of the lubricant-solvent mixture at different proportions of lubricant and solvent, the reactivity of the lubricant composition alone can be derived from the lubricant-solvent measurements.

In this manner, the effect of the lubricant composition's viscosity can be isolated. At low levels of the lubricant, the lubricant composition should have only a small effect on the overall mixture's viscosity. The use of this solvent-based method allows device 10 to test additive components that might normally be solids when used on their own but can be tested in solution with a lubricant. The solvent can be a commercial fuel or a blend of pure components.

Figure 2:
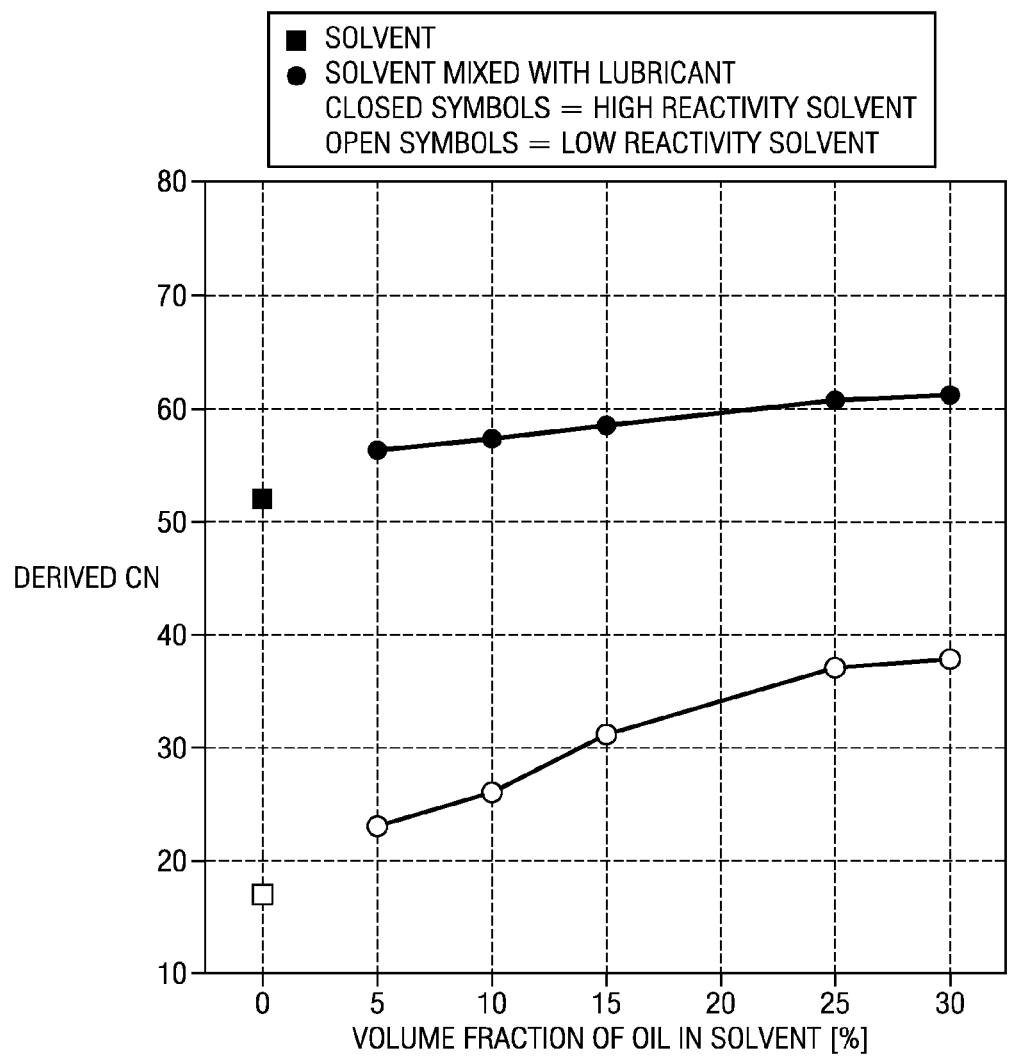
FIG. 2 illustrates the effect on reactivity of different ratios of lubricant-solvent for two different solvents.

FIG. 2 illustrates a plot of a typical lubricant base dissolved in two solvents, a low reactivity solvent (e.g. iso-octane) and a high reactivity solvent (e.g. n-heptane). For each solvent, a range of lubricant-solvent ratios was tested for ignition delay, using device 10. In the example of FIG. 2, this range was 5% to 30% volume fraction of lubricant in solvent.

In the example of FIG. 2, the reactivity index is a derived CN value. However, as explained below, the CN derived from ignition delay is only one example of a "reactivity index". Various other reactivity indexes could be derived from the ignition delay measured by device 10.

As illustrated, the reactivity index (derived CN) is roughly linear with the level of solvent. For each solvent, a regression method may be used to fit a curve to the data. In this manner, the reactivity value at 100% lubricant can be determined.

An alternative to a CN-based reactivity scale is a reactivity index based on both a low reactivity compound (e.g. iso-octane) on one end and a high reactivity compound (e.g. n-heptane or n-hexadecane) on the other. As further explained below, at a fixed condition, the ignition delay of the lubricant composition is correlated to the corresponding mixture to determine the reactivity index. Other solvents, such as 93 RON gasoline and low-sulfur diesel, could also be used as the bounds for this scale.

In this manner, a constant volume combustion device, such as device 10, can be used to measure the reactivity of a lubricant composition to determine its expected contribution to engine knock. The initial conditions of the device 10 mimic the operating parameters of an engine at a certain point in the engine cycle. The proper selection of these conditions can determine the extent to which the knock prediction is faithful to engine-based measurements. A scale, based on two pure solvents can be established to rank the lubricant or lubricant component. The same scale can also be related to knock results from engine-based testing. This enables the identification of improved lubricants for high-performance engines.

Figure 3:
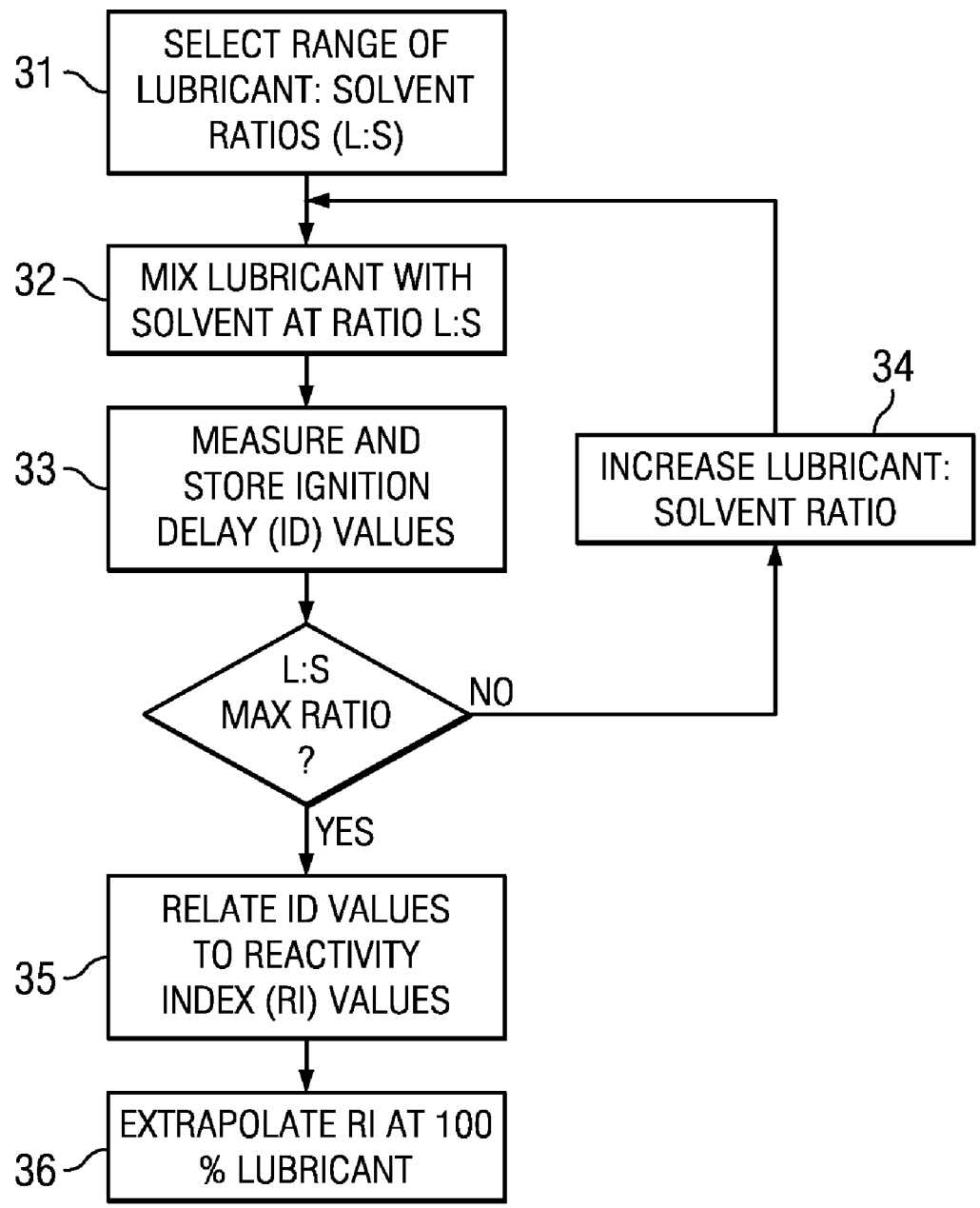
FIG. 3 illustrates a method of using a constant volume combustion device to determine reactivity of a lubricant composition.

FIG. 3 illustrates a method of using a constant volume combustion device to determine reactivity of a lubricant composition. Step 31 is selecting a solvent and a range of lubricant-solvent ratios (L:S). The low end will have a minimal amount of lubricant, such as the 5% ratio in the example of FIG. 2. The high end will be an optimized ratio, depending on the viscosity of the lubricant and the amount of solvent needed to prevent adverse effects on the atomization of the test fluid into the device 10. In the example of FIG. 2, the high end is 30%, but less or more lubricant could be mixed. It is expected that the high end of the ratio will result in a lubricant-solvent mixture having a viscosity comparable to that of diesel fuel. As long as test results are not affected by the mixture viscosity, lubricant percentages greater than 30% may be possible or even desirable.

Step 32 is mixing the lubricant composition with the solvent at a first ratio of the selected range of ratios. Step 33 is using the constant volume combustion device to measure ignition delay (ID) at that ratio. The sample size is small, typically less than 100 mL.

If there remain ratios within the range to be tested, Step 34 is incrementing the ratio, so that a different ratio is next tested. An example of a suitable increment is an additional 5% of the lubricant composition.

After various lubricant-solvent ratios have been tested, Step 35 is relating the ignition delay values associated with those ratios to a reactivity index. Alternatively, as stated above, Steps 31-34 can be repeated for a second solvent, so that the reactivity index is based on measured data from both solvents.

Step 36 is performing a regression analysis or other statistical method to extrapolate the estimated reactivity index for a fluid that is 100% comprised of the lubricant composition with no solvent.

If the test method is performed for two solvents, as in the example of FIG. 2, theoretically, the two curves converge at 100% lubricant. A "best point estimate" could be used to calculate the point of converge.

The reactivity index of the present invention can be obtained in a manner analogous to the reactivity scales associated with ON (octane number) and CN (cetane number) testing. For example, in ON testing, an ON scale is defined by the composition of reference fuel blends. A sample fuel's knock intensity is compared to those of the reference fuel blends. The ON of the reference fuel blend that matches the knock intensity of the sample fuel establishes the ON of the test fuel.

For purposes of the present invention, a similar RI (reactivity index) scale for a reference mixture is determined. As indicated above, the RI can be based on a scale bounded by a low reactivity compound on one end ad a high reactivity compound on the other. For each lubricant-solvent mixture (sample mixture), the result at a given solvent percentage can be compared to a reference mixture. For example, the ignition delay of x % lubricant in a solvent can be matched to the ignition delay of x % of a reference compound in the solvent. If the ignition delay of a 5% lubricant mixture is the same as the ignition delay of a 5% reference mixture, the lubricant can be said to have a similar reactivity to that of the reference.

Thus, a feature of the invention is the ability to compare lubricants of different viscosities. Higher viscosity fluids can result in longer ignition delays as a factor of their viscosity and not as a result of chemistry. The method of the present invention permits the reactivity of a lubricant to be isolated from its viscosity.

In all aspects of the invention, as examples of the base lubricant, the base oil can be a natural oil; the base oil can be derived from coal or shale; the base oil can be a mineral oil; the base oil can be a synthetic oil; the base oil can be a polyalphaolefin oil; the base oil can be a polyester oil; the base oil can be ester based (i.e. Phthalate Esters, Trimallitate Esters); the base oil can be alkylated naphthalenes (AN). The one or more additives can include at least one of an alcohol, an ether, an ester, an organometallic compound, or combination thereof; the one or more additives can include at least one of ferrocene, butyl ferrocene, or combination thereof; the one or more additives can include at least one of ethyl acetate, isoamyl acetate, amyl acetate, isoamyl propionate, isoamyl nonanoate, isobutyl acetate, isobutyl alcohol, methyl butyrate, methyl caproate, methyl caprylate, or combination thereof; the one or more additives can include at least one of cyclopentadienyl manganese tricarbonyl, methylcyclopentadienyl manganese tricarbonyl, ethylcyclopentadienyl manganese tricarbonyl, propylcyclopentadienyl manganese tricarbonyl, indenyl manganese tricarbonyl, methyl indenyl manganese tricarbonyl, fluorenyl manganese tricarbonyl, dimethylcyclopentadienyl manganese tricarbonyl, methylpropylcyclopentadienyl manganese tricarbonyl, phenylcyclopentadienyl manganese tricarbonyl, or combination thereof.

What is claimed is:

1. A test method for testing engine lubricating oils and their additives using a constant volume combustion test device, comprising:
   selecting a sample of a lubricant composition to be tested;
   mixing the lubricant composition with a solvent to reduce the viscosity of the lubricant composition, thereby forming a sample having a predetermined ratio of the lubricant composition to solvent;
   wherein the lubricant composition is a substance under test and the solvent is introduced solely for the purpose of the test method;
   subjecting the sample to a constant volume combustion test to determine the ignition delay associated with the sample;
   associating the ignition delay with a reactivity index;
   repeating the above steps for an iterative range of samples, each sample having a predetermined lubricant-solvent ratios, thereby acquiring an iterative data set of measurement values from the constant volume combustion device, each measurement value having an associated lubricant-solvent ratio;

applying statistical methods to the data set to calculate the reactivity of the lubricant composition without the solvent, without direct measurement of the lubricant composition without the solvent.

2. The method of claim 1, wherein the range of samples have lubricant-solvent ratios of more than 5% and less than 30%.

3. The method of claim 1, wherein the lubricant composition contains a solid dissolved in the solvent.

4. The method of claim 1, wherein the solvent is a solvent from the group of: iso-octane, n-heptane, n-hexadecane, RON gasoline, or low-sulfur diesel.

5. The method of claim 1, wherein the reactivity index is the cetane number.

6. The method of claim 1, wherein the lubricant-solvent mixture has a viscosity less than or comparable to that of diesel fuel.

7. A test method for testing engine lubricating oils and their additives using a constant volume combustion test device, comprising:

selecting a sample of a lubricant composition to be tested;

mixing the lubricant composition with a low reactivity solvent to reduce the viscosity of the lubricant composition, thereby forming a sample having a predetermined ratio of the lubricant composition to the low reactivity solvent;

wherein the lubricant composition is a substance under test and the solvent is introduced solely for the purpose of the test method;

subjecting the sample to a constant volume combustion test to determine the ignition delay associated with the sample;

associating the ignition delay with a reactivity index;

repeating the above steps for an iterative range of samples, each sample having a predetermined lubricant-solvent ratio, thereby acquiring a first iterative data set of measurement values from the constant volume combustion device, each measurement value having an associated lubricant-solvent ratio;

repeating the above steps for a high reactivity solvent, thereby acquiring a second data set of measurement values from the constant volume combustion device; and applying statistical methods to the first data set and the second data set to calculate the reactivity of the lubricant composition without the low reactivity solvent and without the high reactivity solvent, without direct measurement of the lubricant composition without the solvent.

8. The method of claim 7, wherein the range of samples have lubricant-solvent ratios of more than 5% and less than 30%.

9. The method of claim 7, wherein the lubricant composition contains a solid dissolved in the solvent.

10. The method of claim 7, wherein the reactivity index is the cetane number.

11. The method of claim 7, wherein the lubricant-solvent mixture has a viscosity less than or comparable to that of diesel fuel.

12. The method of claim 7, wherein the low reactivity solvent is iso-octane.

13. The method of claim 7, wherein the high reactivity solvent is n-heptane.

14. The method of claim 7, wherein the high reactivity solvent is n-hexadecane.

* * * * *